United States Patent
Kjaer et al.

(10) Patent No.: US 10,159,759 B2
(45) Date of Patent: Dec. 25, 2018

(54) PET TRACER FOR IMAGING OF NEUROENDOCRINE TUMORS

(75) Inventors: Andreas Kjaer, Frederiksberg (DK);
Ulrich Knigge, København Ø (DK);
Liselotte Højgaard, København Ø (DK); Palle Rasmussen, Roskilde (DK)

(73) Assignee: SOMSCAN APS, Frederiksberg (DK)

( * ) Notice: Subject to any disclaimer, the term of this patent is extended or adjusted under 35 U.S.C. 154(b) by 0 days.

(21) Appl. No.: 14/241,958

(22) PCT Filed: Aug. 23, 2012

(86) PCT No.: PCT/DK2012/050305
§ 371 (c)(1),
(2), (4) Date: Jun. 10, 2014

(87) PCT Pub. No.: WO2013/029616
PCT Pub. Date: Mar. 7, 2013

(65) Prior Publication Data
US 2014/0341807 A1 Nov. 20, 2014

Related U.S. Application Data

(60) Provisional application No. 61/529,262, filed on Aug. 31, 2011.

(30) Foreign Application Priority Data

Aug. 31, 2011 (DK) .................... 2011 00654

(51) Int. Cl.
*A61K 51/00* (2006.01)
*A61M 36/14* (2006.01)
*A61K 51/08* (2006.01)
*A61K 51/04* (2006.01)

(52) U.S. Cl.
CPC ........ *A61K 51/088* (2013.01); *A61K 51/0482* (2013.01); *A61K 51/083* (2013.01); *A61K 51/08* (2013.01); *A61K 2121/00* (2013.01); *A61K 2123/00* (2013.01)

(58) Field of Classification Search
None
See application file for complete search history.

(56) References Cited

U.S. PATENT DOCUMENTS

2004/0044177 A1* 3/2004 Macke .................. A61K 38/31
530/311
2007/0025910 A1 2/2007 Norenberg

OTHER PUBLICATIONS

Lewis et al. (Nuclear Med. Biol. 1999, 26, 267-273).*
Kayani et al. (Cancer 2008, 112, 2447-2455).*
Szelecsényi et al. (Appl. Radiat. Isot. 1993, 44, 575-580; abstract provided).*
Anderson et al. (J. Nucl. Med. 2001, 42, 213-221).*
Anderson et al. (J. Nucl. Med. 1998, 39, 1944-1951).*
Lewis et al. (Nucl. Med. Biol. 1999, 26, 267-273).*
Hanaoka et al., "Evaluation of $^{64}$Cu-labeled DOTA-$_D$-Phe$^1$-Tyr$^3$-octreotide ($^{64}$Cu-DOTA-TOC) for imaging somatostatin receptor-expressing tumors", *Ann Nucl Med*, vol. 23, 2009, pp. 559-567.
Højgaard, L., "Nuklearmedicin & kræftbehandling", 27. Danske Medicotekniske Landsmøde (Sep. 2009), Klinisk Fysiologi, Nuklearmedicin og PET, Rigshospitalet & KU SUND & DTU, pp. 1-93.
International Search Report from International Application No. PCT/DK2012/050305 dated Nov. 19, 2012.
Zhang, "$^{64}$Cu-DOTA-Tyr$^3$-c(Cys-Tyr-Trp-Lys-Thr-Cys)-Thr-Lys(cypate)-NH$_2$", *Molecular Imaging Contrast Agent Database (MICAD, National Center for Biotechnology Information*, 2008, pp. 1-4.

* cited by examiner

*Primary Examiner* — Michael G. Hartley
*Assistant Examiner* — Melissa J Perreira
(74) *Attorney, Agent, or Firm* — Mayer Brown LLP

(57) ABSTRACT

There is provided a radiolabelled peptide-based compound for diagnostic imaging using positron emission tomography (PET). The compound may thus be used for diagnosis of malignant diseases. The compound is particularly useful for imaging of somatostatin overexpression in tumors, wherein the compound is capable of being imaged by PET when administered with a target dose in the range of 150-350 MBq, such as 150-250 MBq, preferable in the range of 191-210 MBq.

3 Claims, 4 Drawing Sheets

Specification includes a Sequence Listing.

$^{111}$In-DTPA-octreotide    $^{64}$Cu-DOTATATE

```
                        SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Tyr3-Octreotate
<220> FEATURE:
<221> NAME/KEY: MISC_FEATURE
<222> LOCATION: (1)..(1)
<223> OTHER INFORMATION: Xaa=D-Pheylanine
<220> FEATURE:
<221> NAME/KEY: MISC_FEATURE
<222> LOCATION: (4)..(4)
<223> OTHER INFORMATION: Xaa=D-Trytophan

<400> SEQUENCE: 1

Xaa Cys Tyr Xaa Lys Thr Cys Thr
1               5
```

PET TRACER FOR IMAGING OF NEUROENDOCRINE TUMORS

This application is a National Stage Application of PCT/DK2012/050305, filed 23 Aug. 2012, which claims benefit of Serial No. PA 2011 00654, filed 31 Aug. 2011 in Denmark, and claims benefit of U.S. Provisional Ser. No. 61/529,262, filed 31 Aug. 2011, and which applications are incorporated herein by reference. To the extent appropriate, a claim of priority is made to each of the above disclosed applications.

FIELD OF THE INVENTION

The present invention relates to a radiolabelled peptide-based compound for diagnostic imaging using positron emission tomography (PET). The compound may thus be used for diagnosis of malignant diseases.

BACKGROUND OF THE INVENTION

Known imaging techniques with tremendous importance in medical diagnostics are positron emission tomography (PET), computed tomography (CT), magnetic resonance imaging (MRI), single photon computed tomography (SPECT) and ultrasound (US). Although today's imaging technologies are well developed they rely mostly on non-specific, macroscopic, physical, physiological, or metabolic changes that differentiate pathological from normal tissue.

Targeting molecular imaging (MI) has the potential to reach a new dimension in medical diagnostics. The term "targeting" is related to the selective and highly specific binding of a natural or synthetic ligand (binder) to a molecule of interest (molecular target) in vitro or in vivo.

MI is a rapidly emerging biomedical research discipline that may be defined as the visual representation, characterization and quantification of biological processes at the cellular and sub-cellular levels within intact living organisms. It is a novel multidisciplinary field, in which the images produced reflect cellular and molecular pathways and in vivo mechanism of disease present within the context of physiologically authentic environments rather than identify molecular events responsible for disease.

Several different contrast-enhancing agents are known today and their unspecific or non-targeting forms are already in clinical routine. Some examples listed below are reported in literature.

For example, Gd-complexes could be used as contrast agents for MRI according to "Contrast Agents I" by W. Krause (Springer Verlag 2002, page one and following pages). Furthermore, superparamagnetic particles are another example of contrast-enhancing units, which could also be used as contrast agents for MRI (Textbook of Contrast Media, Superparamagnetic Oxides, Dawson, Cosgrove and Grainger Isis Medical Media Ltd, 1999, page 373 and following pages). As described in Contrast Agent II by W. Krause (Springer Verlag 2002, page 73 and following pages), gas-filled microbubbles could be used in a similar way as contrast agents for ultrasound. Moreover "Contrast Agents II" by W. Krause (Springer Verlag, 2002, page 151 and following pages) reports the use of iodinated liposomes or fatty acids as contrast agents for X-Ray imaging.

Contrast-enhancing agents that can be used in functional imaging are mainly developed for PET and SPECT.

The application of radiolabelled bioactive peptides for diagnostic imaging is gaining importance in nuclear medicine. Biologically active molecules which selectively interact with specific cell types are useful for the delivery of radioactivity to target tissues. For example, radiolabelled peptides have significant potential for the delivery of radionuclides to tumours, infarcts, and infected tissues for diagnostic imaging and radiotherapy.

DOTA (1,4,7,10-tetrakis(carboxymethyl)-1,4,7,10tetraazacyclododecane) and its derivatives constitute an important class of chelators for biomedical applications as they accommodate very stably a variety of di- and trivalent metal ions. An emerging area is the use of chelator conjugated bioactive peptides for labeling with radiometals in different fields of diagnostic and therapeutic nuclear oncology.

There have been several reports in recent years on targeted radiotherapy with radiolabeled somatostatin analogs.

US2007/0025910A1 discloses radiolabled somatostatin analogs primarily based on the ligand DOTA-TOC. The radionucleotide can be (64)Copper and the somatostatin analog may be octreotide, lanreotide, depreotide, vapreotide or derivatives thereof. The compounds of US2007/0025910A1 are useful in radionucleotide therapy of tumours.

US2007/0025910A1 does not disclose (64)Cu-DOTA-TATE. DOTA-TATE and DOTA-TOC differ clearly in affinity for the 5 known somatostatin receptors (SST1-SST2). Accordingly, the DOTA-TATE has a 10-fold higher affinity for the SST2 receptor, the receptor expressed to the highest degree on neuroendocrine tumors. Also the relative affinity for the other receptor subtypes are different. Furthermore, since 177Lu-DOTATATE is used for radionuclide therapy, only 64Cu-DOTATATE and not 64Cu-DOTATOC can be used to predict effect of such treatment by a prior PET scan.

There exists a need for further peptide-based compounds having utility for diagnostic imaging techniques, such as PET.

SUMMARY OF THE INVENTION

The present invention is based on the use of the compound $^{64}$Cu-DOTA-TATE having the formula:

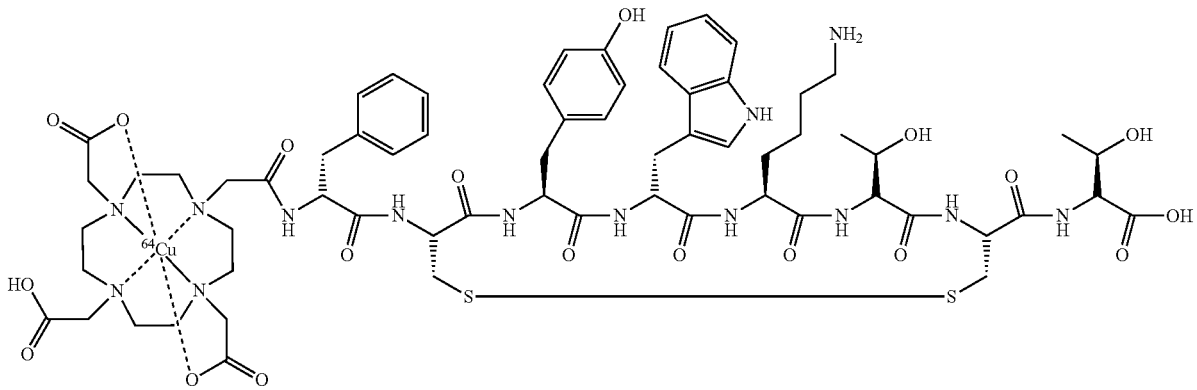

$^{64}$Cu-DOTA-TATE as a PET tracer for better imaging of neuro-endocrine tumors.

The present inventors have surprisingly found that this compound or ligand works better (higher resolution/image quality) than similar analogues for specific PET imaging of somatostatin-expressing tumors (neuroendocrine tumors). Especially, the inventors have found the compound is particularly useful for diagnostic use, when the compound is administered with a target dose in the range of 150-350 MBq, such as 150-250 MBq. The compound is very useful for in vivo diagnosis or imaging, for example by PET, of a neuroendocrine tumor, when the compound is administered with a target dose in the range of 191-210 MBq. This target dose cannot be determined without conducting several clinical trials in human; animal models are not suitable to find this target dose.

The invention also provides use of the compound or a pharmaceutically acceptable salt thereof for the manufacture of a composition for use in a radiographic imaging method, wherein cells or tissues are contacted with the compound; and a radiographic image is made. Preferably, the compound is detected by a gamma camera, positron emission tomography (PET) or single photon emission tomography (SPECT), wherein the compound is administered with a target dose in the range of 150-350 MBq, such as 150-250 MBq, preferable in the range of 191-210 MBq.

The present invention also provides use of the compound or a pharmaceutically acceptable salt thereof in the preparation of a composition for detection of a tumor, tumor tissue, cancer or metastasis in a subject, wherein the compound is administered with a target dose in the range of 150-350 MBq, such as 150-250 MBq. Preferably, the compound of the present invention is used for the manufacture of a radiopharmaceutical for use in a method of in vivo imaging, wherein the compound is administered with a target dose in the range of 191-210 MBq.

In another aspect the present invention provides a method for imaging of somatostatin overexpression in tumors or other tissues comprising administering a compound of the present invention or a pharmaceutically acceptable salt thereof to a subject, wherein the compound is capable of being imaged by PET, detecting somatostatin overexpression in tumors by performing PET, wherein the compound is administered with a target dose in the range of 150-350 MBq, such as 150-250 MBq, preferable in the range of 191-210 MBq.

In still another aspect the present invention provides a method of generating an image of a human body comprising administering a compound of the present invention or a pharmaceutically acceptable salt thereof to said body and generating an image of at least a part of said body to which said compound has distributed using PET, wherein the compound is administered with a target dose in the range of 150-350 MBq, such as 150-250 MBq, preferable in the range of 191-210 MBq.

There is also provided a method of monitoring the effect of treatment of a human body with a drug to combat a condition associated with cancer, preferably a neuroendocrine tumor, said method comprising administering to said body a compound of the present invention or a pharmaceutically acceptable salt thereof and detecting the uptake of said compound by cell receptors, wherein the compound is administered with a target dose in the range of 150-350 MBq, such as 150-250 MBq, preferable in the range of 191-210 MBq.

Additionally, there is provided a method of radiotherapy for the treatment of solid tumors comprising: administering to a mammal harboring a solid tumor, preferably a neuroendocrine tumor, in need of said treatment, an effective dose of a compound of the present invention or a pharmaceutically acceptable salt thereof.

Finally, there is provided a method for manufacturing a compound of Formula I

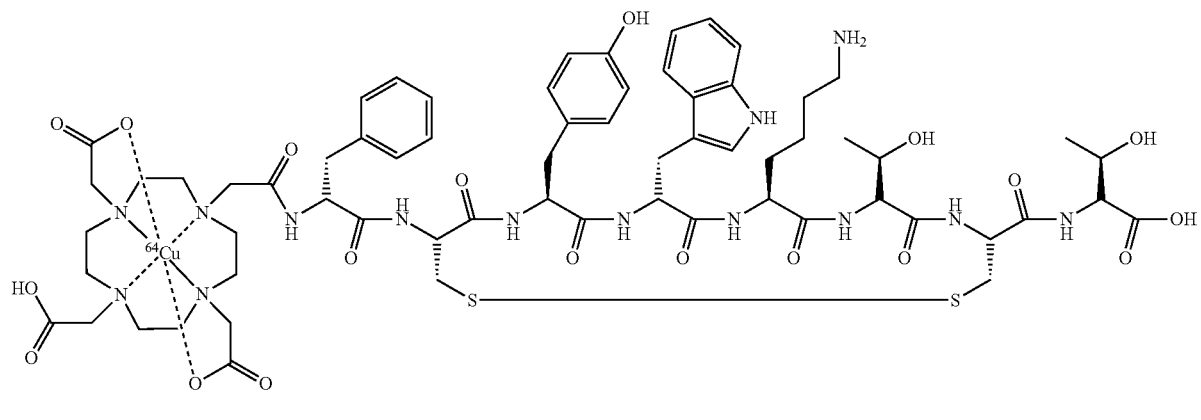

Formula I $^{64}$Cu-DOTA-TATE said method comprising the steps:
- Mixing DOTA-TATE under presence of a scavenger, such as gentisic acid. with a water soluble $^{64}$Cu-salt in an acidic aqueous solution;
- Leaving the solution for at least 2 min;
- Passing the solution through a sterile filter; and
- Recovering the filtered material.

DETAILED DESCRIPTION OF THE INVENTION

Figure 1:
FIG. 1 show PET scans of a patient with intense bowel activity (left lower abdomen).

The invention is now explained in more detail based on an example. Further details may be found in THE JOURNAL OF NUCLEAR MEDICINE•Vol. 53•No. 8•August 2012 Vol. 53, No. 8, August 2012, which is herewith incorporated by reference.

Before explaining the below experimental evidence in more detail it should be noted that the inventors have now clinically tested the $^{64}$Cu-Dotatate-DOTA-TATE complex of the present invention on more than 120 patients with similar results as described below.

EXAMPLE

Preparation of $^{64}$Cu-Dotatate-DOTA-TATE $^{64}$Cu was produced using a GE PETtrace cyclotron equipped with a beamline. The $^{64}$Cu was produced via the $^{64}$Ni (p,n) $^{64}$Cu reaction using a solid target system consisting of a water cooled target mounted on the beamline. The target consisted of $^{64}$Ni metal (enriched to >99%) electroplated on a silver disc backing. For this specific type of production a proton beam with the energy of 16 MeV and a beam current of 20 uA was used. After irradiation the target was transferred to the laboratory for further chemical processing in which the $^{64}$Cu was isolated using ion exchange chromatography. Final evaporation from aq. HCl yielded 2-6 GBq of $^{64}$Cu as $^{64}$CuCl2 (specific activity 300-3000 TBq/mmol; RNP >99%). The labeling of $^{64}$Cu to DOTA-TATE was performed by adding a sterile solution of DOTA-TATE (0.3 mg) and Gentisic acid (25 mg) in aq Sodium acetate (1 ml; 0.4M, pH 5.0) to a dry vial containing 64CuCl2 (~1 GBq). Gentisic acid was added as a scavenger to reduce the effect of radiolysis. The mixture was left at ambient temperature for 10 minutes and then diluted with sterile water (1 ml). Finally, the mixture was passed through a 0.22 µm sterile filter (Millex GP, Millipore). Radiochemical purity was determined by RP-HPLC and the amount of unlabeled 64Cu2+ was determined by thin-layer chromatography. All chemicals were purchased from Sigma-Aldrich unless specified otherwise. DOTA-Tyr3-Octreotate (SEQ ID NO: 1) (DOTA-TATE) was purchased from Sachem (Torrance, Calif.). Nickel-64 was purchased in +99% purity from Campro Scientific Gmbh. All solutions were made using Ultra pure water (<0.07 µSimens/cm). Reversed-phase high pressure liquid chromatography was performed on a Waters Alliance 2795 Separations module equipped with at Waters 2489 UV/Visible detector and a Caroll Ramsey model 105 S-1 radioactivity detector—RP-HPLC column was Luna C18, HST, 50×2 mm, 2.5 µm, Phenomenex. The mobile phase was 5% aq. acetonitrile (0.1% TFA) and 95% aq. acetonitrile (0.1% TFA).

Thin layer chromatography was performed with a Raytest MiniGita Star TLC-scanner equipped with a Beta-detector. The eluent was 50% aq methanol and the TLC-plate was a Silica60 on Al foil (Fluka). Ion exchange chromatography was performed on a Dowex 1×8 resin (Chloride-form, 200-400 mesh).

Patients and Inclusion Criteria

Fourteen consecutively enrolled patients participated in this pilot study and underwent PET scanning with the new tracer on several time points. Patients were eligible in case of a histopathologically confirmed neuroendocrine tumor including positive immunostainings for chromogranin A and synaptophysin. They got offered study inclusion in case of referral to conventional SRI as part of routine follow-up. The maximum allowed time interval between both imaging modalities was 60 days. According to local clinical routine there was no need for interruption of biotherapy e.g. withdrawal of long- or short-time acting somatostatin analogs. However, patients must not have undergone major surgical interventions or systemic chemotherapy between conventional SRI and the PET scanning. The study group consisted of thirteen patients with gastroenteropancreatic neuroendocrine tumors (2 foregut, 6 midgut, 5 NET of unknown origin) and one patient with a known mutation in the multiple endocrine neoplasia I gene, who was diagnosed with a bronchogenic NET ten years ago. Age ranged from 40-80 years. Gender distribution: four women, ten men. Ten of the tumors were active functioning causing classical carcinoid syndromes mainly due to hepatic tumor load. One patient had shown clinical and biochemical manifestations of a Zollinger-Ellison syndrome at time of diagnosis. Twelve patients were in advanced disease state—TNM stage IV according to most recently both UICC/AJCC and ENETS classifications. Two patients had undergone respectively R0- and R1-resections, both without detectable disease so far. Supplementary patient characteristics are given in Table 1. Patient recruiting and follow-up was carried out at the Department of Abdominal Surgery C. SRI was performed at the Department of Clinical Physiology, Nuclear Medicine and PET. Both departments are part of the Neuroendocrine Tumor Center of Excellence, Rigshospitalet, University of Copenhagen, Denmark. All patients had given written informed consent prior to inclusion. The study was approved by the Danish Medicines Agency and the Regional Research Ethics Committee.

TABLE 1

Patient Characteristics

| Patient No. | Primary | Sex | Age at study inclusion (y) | Time since diagnosis (mo) | Primary resected? | Ki67 percentage | Syndrome | TNM* | Metastases | $^{18}$F-FDG |
|---|---|---|---|---|---|---|---|---|---|---|
| 1 | Cecum | M | 56 | 195 | Yes | Not performed | Carcinoid | IV | Carcinomatosis | Positive |
| 2 | Duodenum | F | 50 | 97 | Yes | 1 | Gastrinoma | R0 | | Negative |
| 3 | CUP | M | 44 | 16 | No | 5 | Carcinoid | IV | Peritoneum | Not performed |
| 4 | Ileum | M | 62 | 9 | Yes | 3 | None | R1 | | Not performed |
| 5 | Ileum | M | 63 | 88 | Yes | 3 | Carcinoid | IV | Lymph nodes | Negative |
| 6 | CUP | F | 40 | 23 | No | 5 | Carcinoid | IV | Liver | Negative |

TABLE 1-continued

Patient Characteristics

| Patient No. | Primary | Sex | Age at study inclusion (y) | Time since diagnosis (mo) | Primary resected? | Ki67 percentage | Syndrome | TNM* | Metastases | $^{18}$F-FDG |
|---|---|---|---|---|---|---|---|---|---|---|
| 7 | Pancreas | M | 72 | 2 | No | 7 | None | IV | Liver, bones | Not performed |
| 8 | Lower small intestine | F | 51 | 92 | Yes | 3 | Carcinoid | IV | Liver, breasts | Negative |
| 9 | CUP | M | 81 | 3 | No | 10 | Carcinoid | IV | Liver, peritoneum | Positive |
| 10 | Ileum | M | 64 | 10 | Yes | 1 | None | IV | Lymph nodes | Not performed |
| 11 | CUP | M | 84 | 38 | No | 4 | Carcinoid | IV | Liver | Positive |
| 12 | Ileum | M | 72 | 6 | No | 10 | Carcinoid | IV | Liver, bones, lymph nodes | Not performed |
| 13 | Bronchogenic NET | F | 44 | 103 | No | 5 | Carcinoid | IV | Lungs, lymph nodes | Positive |
| 14 | CUP | M | 76 | 3 | No | 7 | Carcinoid | IV | Liver | Positive |

*TNM stage before study inclusion according to most recent classifications of European Neuroendocrine Tumor Society and American Joint Committee on Cancer/International Union Against Cancer.
R0 resection = complete resection, no microscopic residual tumor: CUP = cancer of unknown primary. R1 resection = microscopic residual tumor.

Image Acquisition

Patients received a target dose of 200 MBq $^{64}$Cu-DOTATATE (range 191-210 MBq). PET-CT images were acquired on an integrated PET-CT Siemens Biograpgh True X, multi-slice. Patients underwent PET scans on at least two times after application of a mean dose of $^{64}$Cu-DOTATATE via an anticubital vene. Imaging was performed 1 h, 3 h and 24 h after injection.

$^{111}$In-pentreotide was intravenously applied with a target dose of 200 MBq. The scans consisted of whole body planar scintigraphy and SPECT-CT: Planar images were acquired at 24 h (anterior and posterior whole-body scan, scan speed 5 cm/min, 512*1.024 matrix) and at 48 h (15 min static planar image (256*256 matrix) of the abdomen using a large field of view medium-energy collimator (Precedence 16-slice scanner, Philips Healthcare; VG Hawkeye, GE Healthcare). SPECT (20 sec/step, 128 angles, 128*128 matrix) over the abdomen was obtained at 24 or 48 h, and included also the chest if a pathological focus was suspected from the whole body scan. A low-dose CT was used as anatomical guide and for attenuation correction. SPECT and CT were fused and reviewed on dedicated workstations (EBW, Philips Healthcare; eNTEGRA, GE Healtcare).

Image Analysis

Planar whole-body scans/ SPECT-CT and PET-CT images were evaluated by two separate teams consisting of both a nuclear medicine physician and a radiologist. Both teams were briefed about the patients past medical history. When abnormal findings only detected on co-registered CT had led the attention to a specific anatomical site, this particular region was revaluated using the molecular imaging data. Judged visually, there also had to be clearly detectable lesion to be accounted as true SRI positive as this was the main focus of interest of the present study. However, all lesions were documented, whether identified on CT images or by SRI. Findings were reported according to their respective anatomical site and if possible absolute numbers of lesions per organ system. All $^{64}$Cu-DOTATATE PET scans where supplemented with contrast enhanced high-dose CT, whereas half of all $^{111}$In-pentreotide SPECT scans were carried out for reasons of radioprotection by only using low-dose CT except if a contrast-enhanced diagnostic CT was ordered by the referring physician. While still remaining blinded to the opposite SRI results, this disparity was tried to balance by additionally providing the team evaluating $^{111}$In-pentreotide SPECT-CT scans with the findings from contrast enhanced diagnostic CT. Interpretation of conventional SRI was performed based on the knowledge of normal tissue accumulation of $^{111}$In-pentreotide. Interpretation of the findings from the new PET method was carried out in a similar manner being aware of possible differences regarding residence times and excretion patterns of the new tracer. Confirmation of the pointed-out lesions was sought by routine follow-up including CT, MRI, conventional SRI and biopsy if possible. Newly detected lesions on co-registered CT imaging were accepted for confirmations as well. Semi-quantitative analysis of tissue radioactivity concentrations was performed by drawing volumes of interests (VOI) around detected lesions and encompassing normal tissues with appreciable tracer uptake on fused PET-CT images. Standardized uptake values (SUV) were automatically calculated and reported only for those lesions with the highest tracer uptake per organ system (including bone and lymph node lesions). $SUV_{MAX}$ is considered a quite reproducible and convenient method for quantitative analysis of PET data. However, this approach is based on SUV calculation considering only the highest image pixel of the target area and might not reflect the normal/average distribution of somatostatin receptors within the respective organ. Moreover, it might be easily biased by erroneous involvement of adjacent tissue with high tracer uptake. We therefore also generated $SUV_{0.5MAX}$ values.

Dosimetry

Radiochemistry and Toxicity

The labeling of 64Cu-DOTATATE took less than 30 min and resulted in greater than 95% yield, as shown with radio-RP-HPLC. No additional radiochemical purification step was required. The amount of unlabeled 64Cu in the product was less than 1%, as demonstrated by radio-TLC. The specific activity of 64Cu-DOTATATE was 4.78 MBq/mmol. The mean 6 SD of the administered mass of 64Cu-DOTATATE was 33.9 6 1.7 ng (range, 31.7-38.0 ng). The mean administered activity was 207 6 10 MBq (range, 193-232 MBq). There were no adverse or clinically detectable pharmacologic effects in any of the 14 subjects, except for 4 who experienced self-limiting nausea of seconds to a few minutes duration immediately after injection. This side effect was probably due to the somatostatin analog contained in the tracer. No significant changes in vital signs were observed.

Biodistribution of 64Cu-DOTATATE

A characteristic imaging series illustrating activity biodistribution at 1, 3, and 24 h after injection is shown in FIG. 1. On the basis of SUV quantitation, tracer accumulation was classified in the following 3 categories: high, moderate, and faint. High accumulation of 64Cu-DOTATATE was seen in the pituitary (averaged SUVmax 6 SEM at 1 h and 3 h, 19.0 6 2.6 and 19.4 6 3.3, respectively), adrenal glands (21.1 6 3.1 and 27.8 6 3.6, respectively), kidneys (21.3 6 2.5 and 19.9 6 2.0, respectively), renal pelvis, and urinary bladder. Moderate to high uptake was observed in the liver (11.3 6 0.8 and 13.6 6 0.8, respectively) and spleen (17.8 6 1.8 and 18.0 6 1.8, respectively). The salivary glands showed faint to moderate uptake in 12 of 14 patients. In 2 patients, moderate tracer accumulation was observed in the thyroid gland, with a diffuse distribution pattern in one patient and a focal pattern in the other. In most patients, numerous lesions were clearly delineated from surrounding tissue (background), showing tracer uptake ranging from moderate to intense (SUVmax range at 1 h and 3 h: liver lesions, 20-81 and 26-81, respectively; bone lesions, 30-117 and 27-111, respectively; and lymph nodes, 9-110 and 9-115, respectively). The TBRs were correspondingly high (1 h and 3 h: liver lesions, 2:1 and 7:1, respectively; bone lesions, 4:1 and 8:1, respectively; and lymph nodes, 3:1 and 19:1, respectively). Background reference SUVmax for lymph nodes was calculated from VOIs drawn over the lumbar part of the psoas muscle, and reference SUVmax for bones was generated by drawing VOIs over contralateral or adjacent normal bone. SUVmax of the early and delayed images remained relatively stable (variability #20%) for tissues that had known high physiologic somatostatin receptor density and did not take part in tracer or activity excretion (i.e., pituitary, adrenals, and spleen). The same was true for most lesions. Conversely, higher time-dependent intrapatient variability for SUVmax was observed for the kidneys, corresponding with urinary tracer excretion as demonstrated by activity accumulation in the renal pelvis and urinary bladder seen only on the early and delayed images. As a possible sign of hepatobiliary excretion, an increase in SUVmax from the 1 h to the 3 h scan in normal liver tissue ranged from 10% to 65% among patients. This finding was in line with visible activity localized to the gallbladder on 3 h images, which was not apparent on images from the early acquisition.

Images of the late scan (24 h) were characterized by activity washout from most organs and lesions, whereas activity retention in the liver and activity accumulation in the intestines became apparent. No activity was visible in the renal collecting system or urinary bladder at the late time point.

Table 2 depicts normalized cumulated activity for source organs. Table 3 shows the associated absorbed dose estimates based on an estimated urinary excretion fraction of 10%, with a presumed 2-h voiding interval and a biologic half-life of 1 h. The dose calculations yielded an effective dose of 0.0315 mSv/MBq. Apart from the pituitary gland, which was estimated to receive an absorbed dose of 0.19 mGy/MBq, the liver was the organ with the highest absorbed dose (0.16 mGy/MBq), followed by the kidneys (0.14 mGy/MBq).

TABLE 2

Organ Normalized Cumulated Activity

| Source organ | Mean (MBq h/MBq) | SE (MBq h/MBq) |
|---|---|---|
| Adrenals | 2.65E−02 | 1.19E−02 |
| Gallbladder | 1.50E−02 | 6.71E−03 |
| Lower large intestine contents | 9.74E−02 | 4.36E−02 |
| Small intestine contents | 5.23E−01 | 2.34E−01 |
| Kidneys | 4.78E−01 | 2.14E−01 |
| Liver | 3.33E+00 | 1.49E+00 |
| Muscle | 4.23E+00 | 1.89E+00 |
| Pancreas | 9.40E−02 | 4.20E−02 |
| Red Marrow | 3.59E−01 | 1.60E−01 |
| Spleen | 2.40E−01 | 1.07E−01 |
| Urinary bladder contents | 1.10E−01 | — |
| Remainder | 7.23E+00 | 3.23E+00 |

TABLE 3

Absorbed Doses

| Target organ | Mean* absorbed dose (mGy/MBq) |
|---|---|
| Adrenals | 1.37E−01 |
| Brain | 1.27E−02 |
| Breasts | 1.32E−02 |
| Gallbladder wall | 3.96E−02 |
| Lower large intestine wall | 4.32E−02 |
| Small intestine | 6.55E−02 |
| Stomach wall | 1.93E−02 |
| Upper large intestine wall | 2.18E−02 |
| Heart wall | 1.86E−02 |
| Kidneys | 1.39E−01 |
| Liver | 1.61E−01 |
| Lungs | 1.67E−02 |
| Muscle | 1.90E−02 |
| Ovaries | 1.92E−02 |
| Pancreas | 9.27E−02 |
| Red marrow | 2.65E−02 |
| Osteogenic cells | 3.35E−02 |
| Skin | 1.22E−02 |
| Spleen | 1.15E−01 |
| Testes | 1.36E−02 |
| Thymus | 1.49E−02 |
| Thyroid | 1.41E−02 |
| Urinary bladder wall | 3.70E−02 |
| Uterus | 1.89E−02 |
| Total body | 2.50E−02 |

*Mean of 5 patients.
Effective dose (mSv/MBq) was 3.15E−02.

Comparative Lesion Detection

Figure 2:
FIG. 2 shows PET scans of patient with metastasis.
Figure 2:
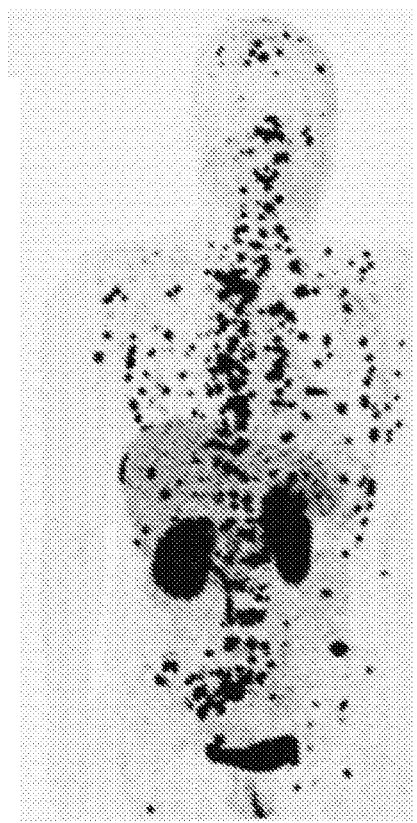

In an organ-based comparison of the 2 SRI modalities, 64Cu-DOTATATE PET detected additional lesions in 6 of 14 patients (43%). All lesions detected on 111In-DTPAoctreotide SPECT were also detected on 64Cu-DOTATATE PET. In 5 patients, the additional lesions were localized in organs or organ systems not previously recognized as metastatic sites: lung lesions (patient 1), a single-bone metastasis and hepatic lesions (liver lesions were known from previously performed CT; patient 8), bone metastases and lymph nodes (patient 9), peritoneal carcinomatosis (patient 12), pancreatic and pulmonary lesions (pulmonary lesions were known; patient 13), and a brain metastasis and a single-bone lesion (patient 14). All foci detected by 64Cu-DOTATATE PET but not by 111In-DTPA-octreotide SPECT were retrospectively assessed as being true-positive lesions, with the exception of the bone lesions in patients 9 and 14. Thus, in these 6 patients, one or more of the additional lesions found by PET were confirmed. 64Cu-DOTATATE PET revealed in general more lesions (n>219, including 98 lymph nodes) than conventional SRI (n>105, including 29 lymph nodes). A common feature of nearly all additionally discovered lesions was their diminutive size (FIG. 2).

Figure 3:
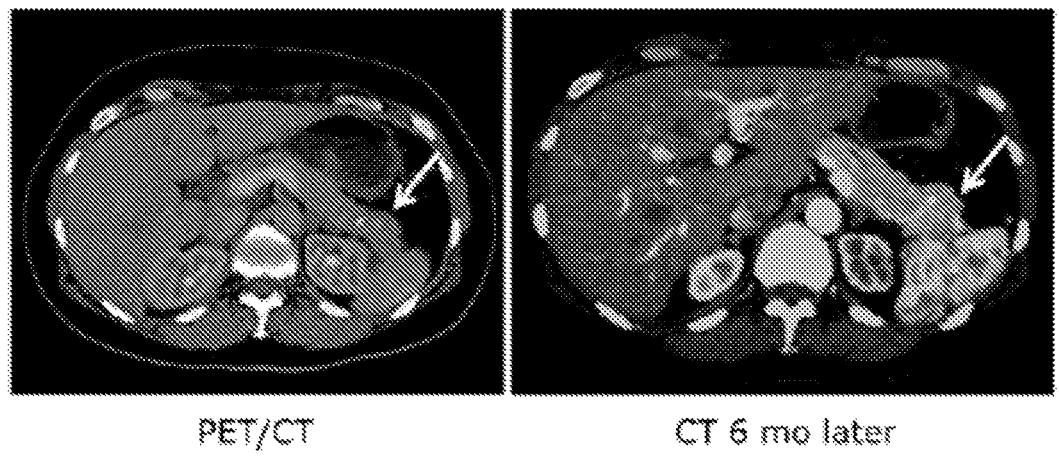
FIG. 3 shows a pancreatic lesions on a $^{64}$Cu-DOTA-TATE PET-CT and on an equivalent contrast enhanced late arterial phase-CT slice obtained 12 months later.
Figure 4:
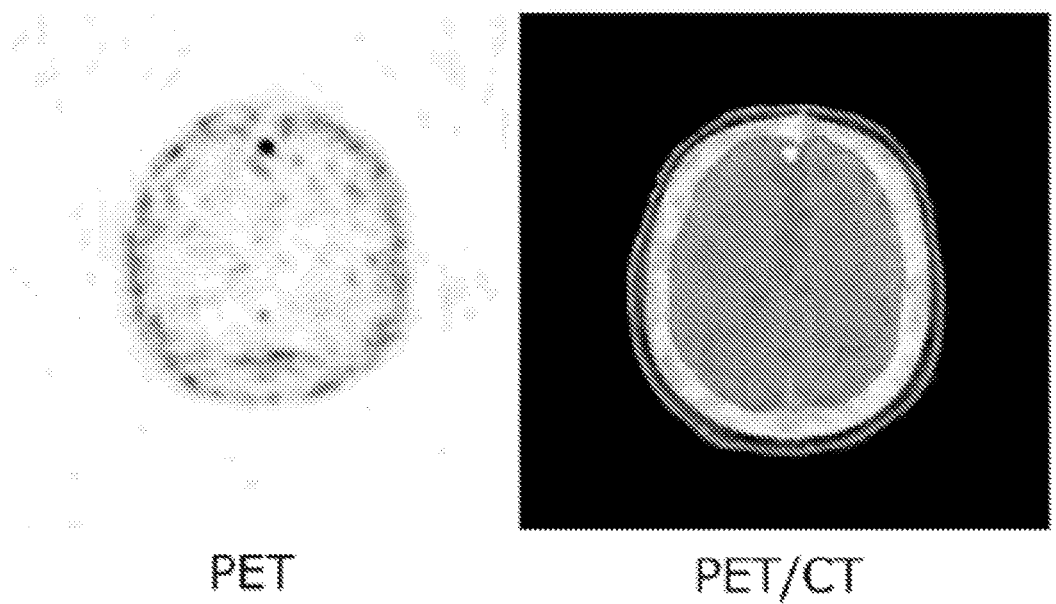
FIG. 4 shows scans of the same cancer patient with neuroendocrine tumors. Left the current gold-standard (111In-octreotide) and right 64-Cu-DOTATATE.

Table 4 gives a more detailed overview of the results from the findings of the 2 SRI modalities, coregistered diagnostic CT, and follow-up imaging. FIG. 3 shows the pancreatic lesions of the patient known with multiple endocrine neoplasia type I syndrome (patient 13) on a 64Cu-DOTATATE PET/CT slice and on an equivalent contrast-enhanced late arterial-phase CT slice obtained 6 mo later. FIG. 4 illustrates the cerebral lesion of patient 14 seen on 64Cu-DOTATATE PET but not on 111In-DTPA-octreotide SPECT.

because it may lead to more accurate staging, which in turn may critically affect the therapeutic management of NET patients. In no case did 111In-DTPAoctreotide SPECT detect lesions that were not also detected by 64Cu-DOTATATE PET. Organ-specific absorbed dose estimates are given in Table 3. On the basis of the dosimetry data for the 5 patients, 64Cu-DOTATATE PET was associated with a lower radiation dose than after a standard administered activity of 111In-DTPA-octreotide.

Despite known shortcomings and the limited number of patients, this result can be considered rather robust. Applying tissue-weighting factors according to IRCP 60 and given the 200-MBq injected activity, we can determine that 64Cu-DOTATATE delivered an estimated effective dose of 6.3

TABLE 4

Number and Localization of Lesions Detected by Different Imaging Methods

| Patient no. | 111In-DTPA-octreotide SPECT | 64Cu-DOTATATE PET | CT | Follow-up* |
|---|---|---|---|---|
| 1 | Peritoneal carcinomatosis, bones (1), lymph nodes (8) | Peritoneal carcinomatosis, bones (>10), lymph nodes (>30) + lungs (6)† | Peritoneal carcinomatosis, bones (1), lymph nodes (>25), lungs (1)† | |
| 2 | Negative | Negative | Negative | |
| 3 | Large solitary peritoneal soft-tissue mass (1) | Large solitary peritoneal soft-tissue mass (1) | Large solitary peritoneal soft-tissue mass (1) | |
| 4 | Negative | Negative | Negative | |
| 5 | Lymph nodes (9) | Lymph nodes (>30) | Lymph nodes (10) | |
| 6 | Liver (6), large solitary peritoneal soft-tissue mass (1) | Liver (>10), large solitary peritoneal soft-tissue mass (1) | Liver (2) | |
| 7 | Pancreas (1), liver (>10), bones (5) | Pancreas (1), liver (>10), bones (>10) | Pancreas (1), liver (>10), bones (1) | |
| 8 | Breasts (>10), large solitary peritoneal soft-tissue mass (1), lymph nodes (1) | Breasts (>10), large solitary peritoneal soft-tissue mass (1), lymph nodes (18) + liver (>10)† + bones (1)† | Breasts (>10), large solitary peritoneal soft-tissue mass (1), hymph nodes (12) + liver (2)† | Bones† |
| 9 | Liver (1), large solitary peritoneal soft-tissue mass (1) | Liver (1), large solitary peritoneal soft-tissue mass (1) + bones (3)† + lymph nodes (2)† | Liver (1) | Lymph nodes‡ |
| 10 | Lymph nodes (8) | Lymph nodes (10) | Lymph nodes (4) | |
| 11 | Liver (>10) | Liver (>10) | Liver (>10) | |
| 12 | Ileum (1), liver (>10), bones (4), lymph nodes (2) | Ileum (1), liver (>10), bones (7), lymph nodes (6) + Peritoneal carcinomatosis† | Ileum (1), liver (>10), lymph nodes (4) | Peritoneal carcinomatosis† |
| 13 | Lymph nodes (1), thyroid gland (1) | Lymph nodes (1), thyroid gland (1) + pancreas (3)† + lungs (4)† | Lymph nodes (3) + lungs (10)† | Pancreas† |
| 14 | Liver (1), large solitary peritoneal soft-tissue mass (1), peritoneal carcinomatosis | Liver (1), large solitary peritoneal soft-tissue mass (1), peritoneal carcinomatosis + brain (1)† + bones (1)† | Liver (1), large solitary peritoneal soft-tissue mass (1), peritoneal carcinomatosis | Brain‡ |

*Confirmation by follow-up with CT (coregistered, stand-alone).
†Additional findings detected by PET method.
‡Bone lesions in patients 9 and 14 have not been confirmed yet.
If lesions were known from previous investigations, confirmation was not demanded (Table 1). Besides abdominal SPECT, thoracic SPECT was performed in patients 1, 5, 7, 8, 10, 11, 13, and 14, Numbers are given in parentheses.

The inventors found that PET with 64Cu-DOTATATE provided considerably better image quality than SPECT with 111In-DTPA-octreotide, resulting in a higher lesion detection rate for 64Cu-DOTATATE PET than for 111In-DTPA-octreotide SPECT. In 5 patients (36%), 64Cu-DOTATATE PET revealed lesions in organs not previously known as metastatic sites. This finding is of special interest mSv to the patients, compared with 12 mSv for 111In-DTPA-octreotide for a standard administered activity.

Conventional SRI with 111In-DTPA-octreotide usually follows a 2 d protocol. In contrast, the time required for SRI is considerably reduced when using 64Cu-DOTATATE because of the accelerated imaging procedures offered by the physical and pharmacokinetic features of this tracer.

As shown herein, image acquisition can be initiated at 1 h after administration of 64Cu-DOTATATE. High spatial resolution was illustrated by sharp images, allowing for distinct delineation of small organs with appreciable somatostatin receptor expression such as the adrenals and the pituitary. High image contrast could be demonstrated by notably high TBRs, even in organs with physiologic high somatostatin receptor density such as the pancreas. In accordance with this is the detection of an additional pancreatic lesion (TBR, 6:1) in patient 13 with known multiple endocrine neoplasia type I syndrome.

Despite enhanced clinical awareness and a consecutive diagnostic exploration by endoscopic ultrasonography, validation of the lesion shown on PET was not achieved until 6 mo later by contrast-enhanced CT, demonstrating a lesion size of 6 mm. Obvious advantages of PET systems, such as enhanced photon sensitivity and reduced acquisition times, have paved the way for the clinical implementation of positron emitter-linked somatostatin analogs. Furthermore, the spatial resolution achievable by PET is generally higher than that by SPECT. However, a limiting factor for high-resolution PET is the positron energy of the used isotope.

The use of isotopes with a lower positron energy is therefore considered advantageous and may result in reduced image blurring because of correspondingly shorter positron ranges. That impact is considered to be modest in human state-of-the art whole-body PET scanners with intrinsic spatial resolution on the order of 4-6 mm in full width at half maximum. However, the impact of positron energy may become more decisive as PET scanner technology continues to advance.

tacting cells or tissues with a compound of Formula I or a pharmaceutically acceptable salt thereof

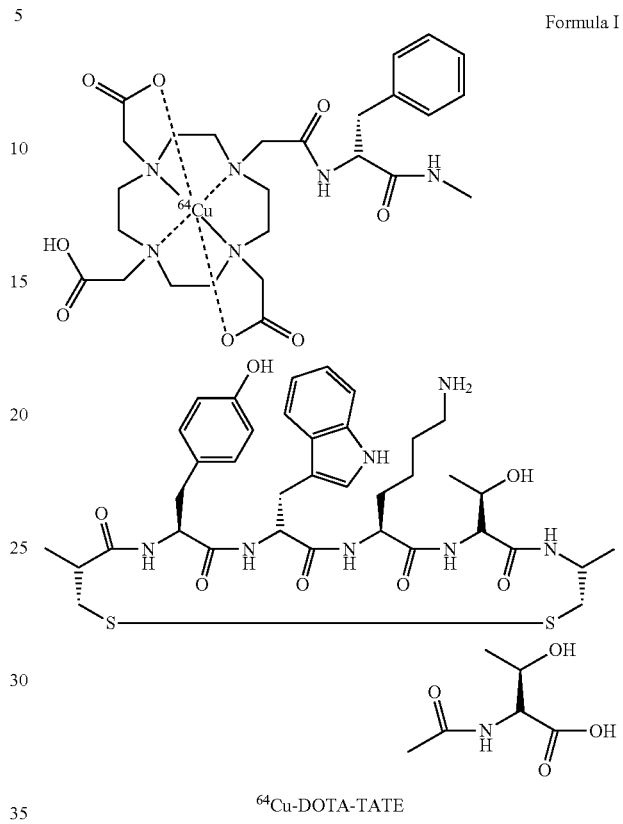

Formula I $^{64}$Cu-DOTA-TATE

The invention claimed is:

1. A method of diagnosing a neuroendocrine tumor in a radiographic imaging method, the method comprising contacting cells or tissues with a compound of Formula I or a pharmaceutically acceptable salt thereof wherein the compound is administered with a target dose in the range of 150-250 MBq, and making a radiographic image for detecting the compound.

2. A method of claim 1, wherein the compound is administered with a target dose in the range of 191-210 MBq.

3. A method of claim 1, wherein the compound is detected by a gamma camera, positron emission tomography (PET), or single photon emission tomography (SPECT).

\* \* \* \* \*